(12) United States Patent
Ruohonen et al.

(10) Patent No.: US 7,925,066 B2
(45) Date of Patent: Apr. 12, 2011

(54) METHOD AND APPARATUS FOR CORRECTING AN ERROR IN THE CO-REGISTRATION OF COORDINATE SYSTEMS USED TO REPRESENT OBJECTS DISPLAYED DURING NAVIGATED BRAIN STIMULATION

(75) Inventors: Jarmo Ruohonen, Vantaa (FI); Perttu Sipilä, Helsinki (FI); Raine Hurme, Helsinki (FI); Risto Ilmoniemi, Espoo (FI); Jari Karhu, Kuopio (FI)

(73) Assignee: Nexstim Oy, Helsinki (FI)

( * ) Notice: Subject to any disclaimer, the term of this patent is extended or adjusted under 35 U.S.C. 154(b) by 882 days.

(21) Appl. No.: 11/853,256

(22) Filed: Sep. 11, 2007

(65) Prior Publication Data
US 2008/0064950 A1 Mar. 13, 2008

Related U.S. Application Data

(60) Provisional application No. 60/825,462, filed on Sep. 13, 2006.

(51) Int. Cl.
*G06K 9/00* (2006.01)
*A61N 1/00* (2006.01)
(52) U.S. Cl. .......................... 382/128; 382/291; 600/13
(58) Field of Classification Search .................. 382/128, 382/129, 130, 131, 132, 133, 134, 168, 181, 382/199, 232, 255, 274, 276, 291, 305, 312; 600/9, 410, 13; 378/21, 68
See application file for complete search history.

(56) References Cited

U.S. PATENT DOCUMENTS

| | | | | |
|---|---|---|---|---|
| 6,490,473 | B1 * | 12/2002 | Katznelson et al. | 600/410 |
| 6,594,516 | B1 * | 7/2003 | Ruohonen | 600/410 |
| 6,827,681 | B2 * | 12/2004 | Tanner et al. | 600/9 |
| 7,087,008 | B2 * | 8/2006 | Fox et al. | 600/13 |
| 2003/0050527 | A1 * | 3/2003 | Fox et al. | 600/13 |
| 2005/0234286 | A1 * | 10/2005 | Riehl et al. | 600/9 |
| 2008/0058581 | A1 * | 3/2008 | Aho | 600/13 |

FOREIGN PATENT DOCUMENTS

GB 2391814 A 2/2004

OTHER PUBLICATIONS

"Non-invasive functional brain mapping using registered transcranial magnetic stimulation" Proceedings of the IEEE Workshop on Mathematical Methos in Biomedical Image Analysis, XX, XX, Jun. 21, 1996, pp. 32-41, Section 3.3.2.

(Continued)

*Primary Examiner* — Seyed Azarian
(74) *Attorney, Agent, or Firm* — Seppo Laine Oy

(57) ABSTRACT

An error in the co-registration of a coordinate system used to represent a head of a subject in image data with a coordinate system used to represent the location of trackers affixed to the scalp surface of the head and a tracked device, such as a transcranial magnetic stimulation ("TMS") induction coil device, is corrected using information representative of the actual distance between the tracked device and the scalp of the subject, such that representations of the tracked device and the subject's head are accurately shown on a display of a navigated brain stimulation ("NBS") system tracking movement of the tracked device in relation to the subject's head. The correction of the error in the co-registration is performed without collecting additional tracking information from trackers on a tracked TMS coil device and the head, which avoids interrupting NBS using the TMS coil device.

35 Claims, 2 Drawing Sheets

OTHER PUBLICATIONS

"Stimulation Methods" International Journal of Computer Assisted Radiology and Surgery; A Journal for Interdisciplinary Research, Development and Applications of Image Guided Diagnosis and Therapy, Springer-Verlag, BE, vol. 1, No. 7, May 18, 2006, pp. 137-145.

Ruohonen J. et al., "Modeling of the Stimulating Field Generation in TMS," Electroencephalography and Clinical Neurophysiology Supplement, vol. 51 (1999).

Ravazzani, P., et al., "Magnetic stimulation of the nervous system: induced electric field in unbounded, semi-infinite, spherical, and cylindrical media," Annals of Biomedical Engineering 24: 606-616, 1996.

* cited by examiner

METHOD AND APPARATUS FOR CORRECTING AN ERROR IN THE CO-REGISTRATION OF COORDINATE SYSTEMS USED TO REPRESENT OBJECTS DISPLAYED DURING NAVIGATED BRAIN STIMULATION

CROSS REFERENCE TO RELATED APPLICATION

This application claims the benefit of U.S. Provisional Application No. 60/825,462 filed Sep. 13, 2006, assigned to the assignee of this application and incorporated by reference herein.

FIELD OF THE INVENTION

The present invention relates generally to transcranial magnetic stimulation and, more particularly, to displaying an accurate representation of a transcranial magnetic stimulation induction coil in relation to the head of a subject during navigated brain stimulation.

BACKGROUND OF THE INVENTION

Transcranial magnetic stimulation ("TMS") uses an induction coil in which a time-varying magnetic field is generated to induce an electric field ("E-field") within the brain. Neurons at the locations of the brain exposed to a strong enough E-field will become activated, or stimulated. In navigated brain stimulation ("NBS"), the E-field induced in the brain by a TMS induction coil device is shown as an overlay on a graphical display of an anatomical representation of the subject's brain. By viewing the display, a user can visualize the E-field induced on the brain and, therefore, interactively position the TMS coil device, in real time, in relation to the brain to stimulate a target site on the brain.

The following data acquisition and processing steps are typically performed as part of NBS.

1. A segmented data representation of the scalp or head surface of a subject is generated from data representative of the anatomical configuration of the subject's head. Typically, data representative of two-dimensional ("2D") magnetic resonance imaging ("MRI") images of the head of the subject, which was previously obtained using conventional MRI techniques, and where the images include at least the brain, upper parts of the skull and attached tissue and cartilage, are processed, using well known software algorithms, to generate a volumetric, three-dimensional ("3D") representation of the head. The 3D representation of the head is then further processed, also using well known software algorithms, to generate a segmented data representation of the head surface of the subject.

2. Tracking elements are implemented to provide that the location and orientation of a TMS coil device with respect to a subject's head can be tracked. As conventional in the art, easily identifiable, reflective markers (trackers) are placed on selected points on the subject's head and also on the TMS coil device to permit automatic recording of the coordinates of the points in 3D. When the coordinates of at least three such points on the head and at least three such points on the TMS coil device have been recorded, the coordinate values for all six degrees of freedom of these objects have been determined. For example, the trackers on the TMS coil device may be a part of a tracking device attached to the TMS coil device, as described in U.S. patent application for TRANSCRANIAL MAGNETIC STIMULATION INDUCTION COIL DEVICE WITH ATTACHMENT PORTION FOR RECEIVING TRACKING DEVICE, Ser. No. 11/847,511 filed Aug. 30, 2007, assigned to the assignee of this application and incorporated by reference herein. The coordinates of the trackers are recorded using a special-purpose camera, as conventional in the art.

3. A co-registration procedure is performed, which correlates data representative of the positions of the trackers on the TMS coil device and the subject's head during a tracking calibration with the image data from which the 3D representation of the subject's head is generated. Typically, in a tracking calibration, several landmark points on the head at which reflective trackers are positioned, such as points on each ear and the nose, are pinpointed on the 2D MRI images or, if available, the volumetric 3D image of the head. The same points are also pinpointed on the subject's head by use of a digitization pen tracker, which also includes reflective trackers. Tracking data representative of the positions of the trackers on the TMS coil device and the subject's head when each of the points are pinpointed by the pen tracker are then collected. After performing such point-to-point correspondences or point-to-point matching, a transformation is computed that aligns the coordinate system used to represent the head in the MRI image data with the coordinate system used to represent the relative positions of the trackers during the calibration. The quality of the transformation can be enhanced, for example, at least in the least-squares sense, by performing additional point-to-point matching which, in turn, improves the accuracy of NBS.

4. On an NBS display, the following are typically shown: a graphical representation of the TMS coil device, in particular preferably only the casing of the TMS coil device in which the coil windings are contained, in relation to a graphical representation of the scalp; a graphical representation of a portion of the brain at a selected depth; and the E-field induced on the brain portion by the TMS coil device as an overlay on the representation of the brain portion. The display, thus, provides the user with a visual representation of the position and orientation of the casing, and thus the coil windings of the TMS coil device, in relation to the head and the brain, and also the E-field induced in the brain, as the user navigates the TMS coil device in relation to the subject's head. The quality of the transformation computed in the co-registration (3. above) affects the accuracy of the representations shown on the display and, thus, the navigation accuracy. As is well known in the art, the E-field induced by the coil windings is computed using a head-shape or head-conductivity-distribution model, e.g., a spherical model, such as described in Ravazzani, P., et al., "Magnetic stimulation of the nervous system: induced electric field in unbounded, semi-infinite, spherical, and cylindrical media," *Annals of Biomedical Engineering* 24: 606-616, 1996, incorporated by reference herein, and based on a model of the shape and location of the copper windings inside the casing of the TMS coil device. The E-field is typically shown on the representation of the brain portion using colors to indicate E-field strength, which aid the user in navigating the TMS coil device to stimulate target sites on the brain portion. The accuracy of the representation of the brain portion, in a large part, determines the accuracy of the representation of the E-field induced on the brain portion shown on the display and, thus, greatly impacts the accuracy with which the user can navigate the TMS coil device to stimulate target sites on the brain.

Prior art co-registration techniques, however, are prone to errors, which can cause inaccuracies in the display of the position of the TMS coil device and the resulting E-field on the NBS display and, thus, cause inaccuracies during NBS.

The most critical sources of error in co-registration are the following.

1. Inaccurate matching of the physical head shape and the MRI images. MRI image data collection typically includes a geometrical distortion that affects the detected head shape. For example, the geometric distortion may cause a perfect sphere to appear as an ellipsoidal on a display. In addition, data segmentation of the MRI image data may not precisely identify the scalp, because of inaccuracies in the MRI image data in the gray level values of the voxels representing points near the scalp surface. As currently obtainable MRI image data typically only has enough resolution to provide for the generation of a 3D representation of the head volume using 1 mm×1 mm×1 mm voxels, the obtainable voxel size limits the accuracy of the MRI image data representative of only the head. In addition, the MRI data includes other inaccuracies that are sources of the geometrical distortion.

2. Trackers on the head move with respect to the head during the NBS procedure. If the trackers on the head move with respect to the head, the co-registration is invalidated and must be repeated. Movement of the trackers on the head may not be detected when a patient is undergoing a NBS procedure using a TMS coil device. For ordinary NBS patient procedures, it is not feasible or practical to fix the trackers to the head of the patient, which may require screwing the trackers into the head.

3. Point-to-point matching is not possible. As the MRI image data has limited resolution, for example, providing for a volumetric representation of the head where the voxels are 1×1×1 mm$^3$, it is very difficult, if not impossible, to pinpoint exactly the same points on the head and also on the volumetric head representation generated from the MRI image data. The inaccuracy in the selection of landmark points during a tracking calibration leads to navigation errors during NBS.

Inaccurate matching of the MRI image data with the subject's head, and inaccurate navigation of the TMS coil device in relation to the head, are readily visible on an NBS display. For example, during NBS, a user of the TMS coil device normally places the TMS coil device so that its casing touches the scalp during stimulation. When the user places the TMS coil device on the scalp, with the outer surface of the casing of the TMS coil device touching the scalp, the TMS coil device should appear to touch the scalp, where the coordinate system used to represent the positions of the trackers on the TMS coil device and the head is accurately co-registered with the coordinate system for the MRI image data representative of the head. The above-mentioned errors in co-registration, however, typically cause the TMS coil device to appear on the NBS display either above the scalp or inside the head, the latter of which is impossible.

It is undesirable to stop an NBS procedure, and repeat the collection of tracking information from the trackers as part of another tracking calibration, such that another transformation can be performed and, therefore, provide that the NBS display shows the TMS coil device in relation to the head based on an updated co-registration.

Therefore, there exists need for correcting an error in the co-registration of a coordinate system used to represent the head in the MRI image data with the coordinate system used to represent the position of trackers on the head and a TMS coil device, without collecting additional tracking data following a tracking calibration.

SUMMARY OF THE INVENTION

In accordance with the present invention, a controller of an NBS system performs a co-registration, which correlates a coordinate system used to represent the head of a subject in image data with a coordinate system used to represent the location of trackers affixed to the head surface of the subject and a tracked device, such as a TMS coil device, and corrects errors in co-registration data using information representative of the actual distance between the tracked device and the scalp of the subject.

In one embodiment, the distance information is supplied to the controller while a user, using the NBS system display, (i) operates a tracked, TMS coil device to stimulate target sites on the brain ("online mode"), or (ii) moves the TMS coil device in relation to the head without stimulating the brain ("offline mode"). The controller corrects an error in the co-registration data, based on the distance information, in the online mode or offline mode.

In another embodiment, the user of the tracked device, such as a TMS coil device or pointer pen, supplies the distance information to the controller, based on observations of the position of the tracked device in relation to the scalp on a display of the NBS system, in relation to the actual position of the tracked device on the scalp.

In still another embodiment, the tracked device is a TMS coil device including a proximity sensor on its casing that determines the distance between the TMS coil device and the scalp and supplies the distance to the controller of the NBS system.

In a further embodiment, the controller corrects an error in the co-registration data, based on the fact that the tracked device cannot even partially be inside the head, and the distance information does not include an actual distance measurement.

In another embodiment, the controller instructs the user of the tracked device to maintain the tracked device in contact with the scalp, and corrects the co-registration based on the distance between the tracked device and the scalp being zero.

BRIEF DESCRIPTION OF THE DRAWINGS

Other objects and advantages of the present invention will be apparent from the following detailed description of the presently preferred embodiments, which description should be considered in conjunction with the accompanying drawings in which like references indicate similar elements and in which.

DETAILED DESCRIPTION OF THE INVENTION

In NBS, a display typically shows the position of a TMS coil device in relation to the scalp of a subject, while the user moves the TMS coil device to stimulate target sites on the brain. See, for example, U.S. Pat. No. 6,827,681, incorporated by reference herein. To generate such a display, a coordinate system used to represent the head of the subject in image data, such as MRI image data, is correlated with a coordinate system used to represent the positions of trackers on the TMS coil device and the head, using algorithms for transforming different coordinate systems into a single co-registered coordinate system well known and conventional in the art.

Figure 1:
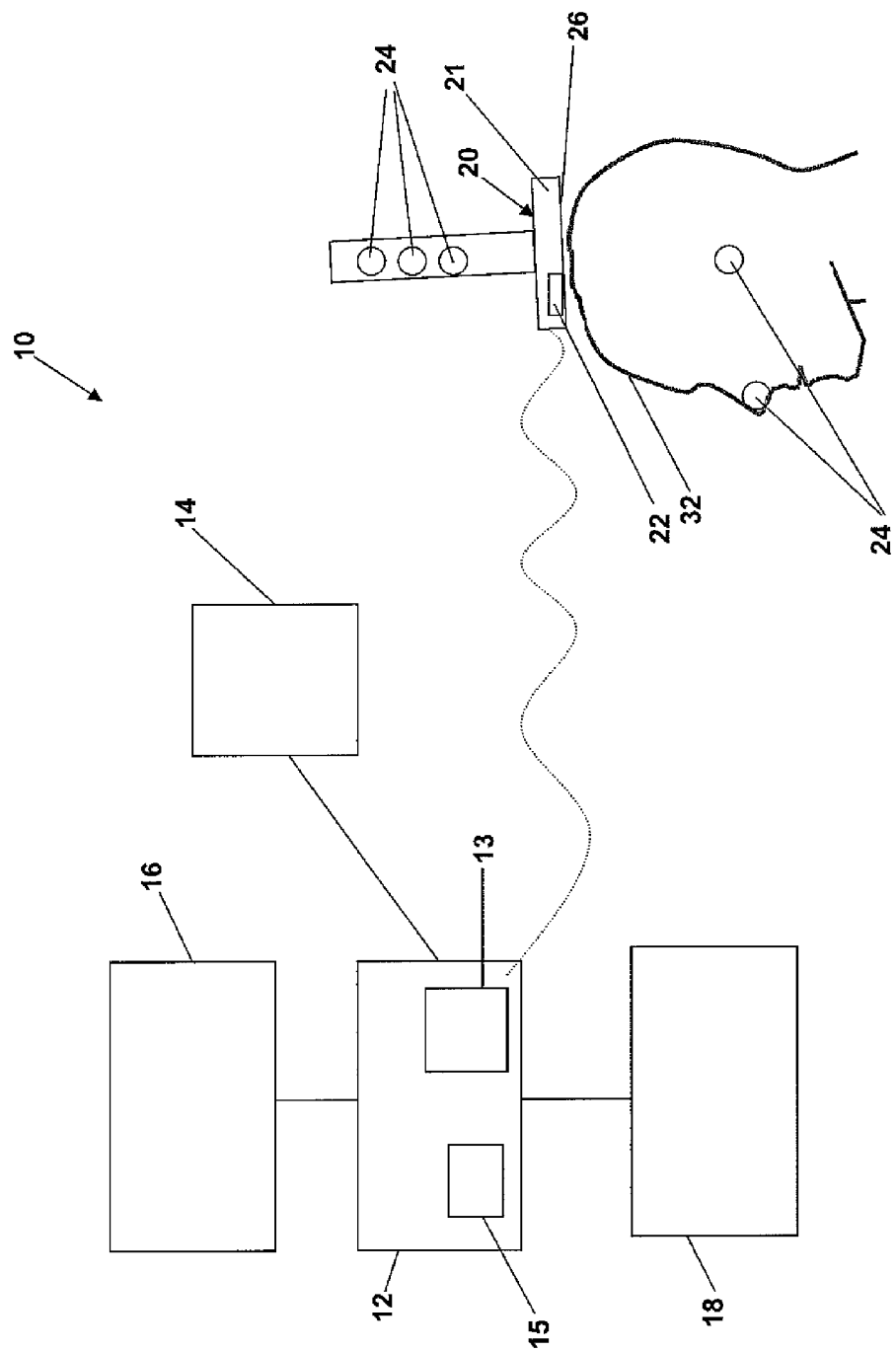
FIG. 1 is a functional block diagram of an exemplary navigated brain stimulation system for correcting an error in co-registration data, in accordance with the present invention.

FIG. 1 illustrates an exemplary NBS system 10 that correlates coordinate systems used to generate representations of objects shown on an NBS display, such as, for example, a TMS coil device, a head and the scalp of the head, while a user moves the TMS coil device to stimulate target sites on the brain of the subject and, in accordance with the present invention, corrects an error in co-registration data using information representative of the distance between a device whose movement is tracked by the NBS system 10, such as, for example, a TMS coil device 20 of the NBS system 10, and the scalp, without requiring the collection of additional tracking data from trackers on the tracked device so that an additional tracking calibration can be performed. Referring to FIG. 1, the system 10 includes an NBS controller 12 coupled to an input device 14, a display 16 and a tracking camera system 18. In addition, the TMS coil device 20 includes an optional proximity sensor 22. Also, the system 10 includes trackers 24 placed at predetermined locations on the TMS coil device 20 and head 30 of a subject.

The input device 14 is a conventional data entry device, such as a keyboard, mouse or speech recognition device, from which data can be supplied to the controller 12.

The display 16 is a conventional graphical display device, such as a CRT monitor, LCD or plasma screen, which receives and then generates a graphical display from display data supplied from the controller 12.

The tracking camera system 18 is a conventional tracking system including an infrared transceiver that transmits IR energy signals and detects the reflections of the transmitted IR signals by the reflective trackers 24, which are positioned on the head 30 and the TMS coil device 20 and also on a conventional digitization pen tracker (not shown). Based on data representative of the reflections detected at the IR transceiver when selected points on the head 30 are pinpointed using the digitization pen during a tracking calibration, and data representative of the shape of the casing 21 of the TMS coil device 20 and the shape of the scalp 32, the processor of the system 18, using conventional techniques in the art, determines the locations of the trackers 24 on the TMS coil device 20 in relation to the trackers 24 on the head 30, and stores information representative of the determined locations using a predetermined coordinate system. Alternatively, the controller 12 processes the reflection data to determine the locations of the trackers 24 and uses the predetermined coordinate system to represent of the positions of the trackers 24 on the TMS coil device 20 and the head 30 during the tracking calibration. In addition, the tracking system 18 continuously generates and supplies to the controller 12, during NBS operation, tracking data representative of the positions of the TMS coil device 20 and the head 30 using the predetermined coordinate system.

The TMS coil device 20 is a conventional induction coil winding device including a casing 21 containing coil windings (not shown). The casing 21 has a bottom outer surface 26 that is placed upon or adjacent to the scalp 32 to perform TMS.

The controller 12 is a conventional processor coupled to a memory (not shown) and includes a conventional wireless data communication device 13 and a conventional audio generator 15. The processor performs software algorithms encoded in the memory to control data exchange with the wireless device 13, the audio generator 15, the display 16, the tracking camera system 18 and the input device 14. In addition, the controller 12 performs conventional processing to generate graphical representations of the head 30, scalp surface 32 of the head 30 and the TMS coil device 20 for display on the display 16, to identify the position of the TMS coil device 20 in relation to the head 30 and the scalp 32 and to provide for display of the representations of the head 30 and the TMS coil device 20 in relation to each other on the display 16. Further, the controller 12 optionally performs a tracking calibration using tracking data supplied by the tracking system 18, and a co-registration to correlate the coordinate systems used to represent head in the MRI image data and the position of the TMS device 20 in relation to the head 30 based on the tracking data. See, for example, Ruohonen J. et al., "*Modeling of the stimulating field generation in TMS*," Electroencephalography and Clinical Neurophysiology Supplement vol. 51 (1999) and Ravazzani P. et al., "*Magnetic stimulation of the nervous system: induced electric field in unbounded, semi-infinite, spherical, and cylindrical media*," Annals of Biomedical Engineering 24: 606-616 (1996), incorporated by reference herein, for a description of co-registration techniques.

In accordance with the present invention, during or following co-registration of a coordinate system used to represent the positions of the trackers 24 pinpointed during a tracking calibration with a coordinate system used to represent a head in MRI image data from which a volumetric image of the head can be generated, the controller 12 corrects an error in co-registration data using information representative of the distance between the outer surface 26 of the casing 22 of the TMS coil device 20 and the scalp surface 32. The distance information is supplied to the controller 12 by a user via the input device 14, or automatically by the proximity sensor 22.

Figure 2:
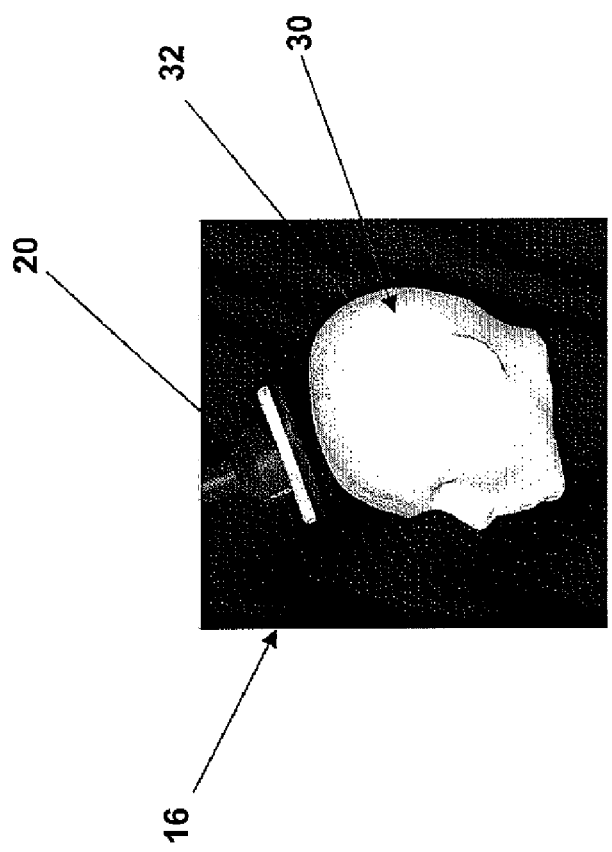
FIG. 2 is a cross-sectional view of an exemplary NBS display showing a TMS coil device incorrectly positioned above the scalp of a subject, based on an error in the co-registration data.

In one embodiment, a user using the NBS system 12 to perform NBS with the TMS coil device 20 moves the TMS coil device 20 with respect to the head 30 and views the display 16, such as shown in FIG. 2, to determine whether the location of the TMS coil device 20 shown on the display 16 is the same as that which the user observes directly. When the user physically moves the TMS coil device 20 to cause the outer surface 26 to contact the scalp 32, the user precisely knows the actual, correct location of the TMS coil device 20 with respect to the scalp 32 and the distance between the former and latter is zero. Thus, when the TMS coil device 20 is shown on the display 16 above the scalp 32 or within the head when the TMS coil device 20 is actually positioned touching the scalp 32 by the user, the co-registration data contains an error. To correct the error, the user at the input device 14 supplies information to the controller 12 representative of the distance between the TMS coil device 20 and the scalp 32. The actual distance is zero while the user maintains the TMS coil device 20 positioned so that a point on the outer surface 26 physically touches the scalp 32.

Figure 3:
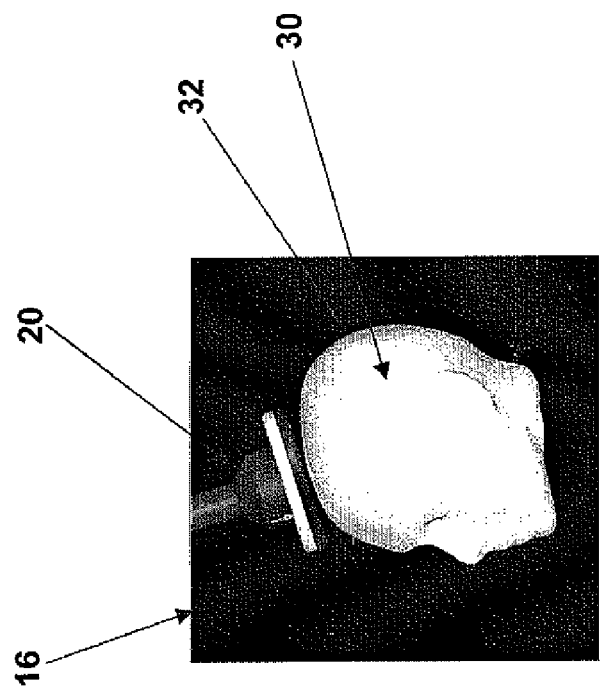
FIG. 3 is a cross-sectional view of the subject of FIG. 2 on the NBS display following correction of an error in the co-registration data, in accordance with the present invention.

In one embodiment, the user enters a "1" as an error notice at the device 14 while maintaining a point on the outer surface 26 of the TMS coil device 20 directly touching the scalp 32, and while the NBS display 16 shows the TMS coil device 20 above or below the scalp 32. When the controller 12 receives the "1" data signal, the controller 12 performs a process to correct the co-registration data for the point at which the TMS device 20 is currently located in relation to the head 30. Following correction of the co-registration data for such point, the display 16 shows the TMS coil device 20 positioned correctly, directly on the scalp 32, as shown in FIG. 3.

In an exemplary embodiment, when the user transmits the error notice to the controller 12, the controller 12 determines the position of the TMS coil device 20 in relation to the scalp 32 based on tracking data supplied from the tracker system 18 and acquired at the same or substantially the same time as the error notice transmission by the user. The controller 12 then performs processing to match the position of the TMS coil device 20 represented by the tracking data acquired contemporaneously with the error notice transmission to a point in the co-registration data precisely on the scalp 32, updates the registration data for the point based on such matching, and then refreshes the display 16 to show the representation of the TMS coil device 20 directly on the scalp 32 based on the updated co-registration data.

As the user continues to perform TMS, additional corrected co-registration data points may be computed, which increases the overall accuracy of the co-registration and, thus, the accuracy with which the TMS coil device 20 is represented in relation to the head 30 on the display 16. The corrected co-registration data is preferably saved in a patient file in the memory of the controller 12, such that the corrected co-registration data and location coordinates and orientation information of the TMS coil device 20 in relation to the scalp 32 and the brain are available for future TMS procedures performed using the NBS system 10.

In another embodiment, the distance information and the position of the TMS coil device 20 at the time the distance information was generated are saved in the memory of the controller 12 and are accessible to correct co-registration data while the user is not operating the TMS coil device 20 to stimulate the brain ("offline mode").

Advantageously, the NBS system 10 corrects an error in the co-registration data while the user continues to perform NBS using the TMS coil device 20 ("online mode"). The user does not need to correct an error in the co-registration before commencing use of the NBS system 10 to perform TMS using the TMS coil device 20, or perform another tracking calibration, which requires the collection of additional tracking data and stopping any ongoing TMS procedure being performed using the NBS system 10, when an error in the co-registration is detected in the online mode. When the controller 12 is notified of the error, in other words, the distance information is supplied to the controller 12, the NBS system 10 corrects the error in the co-registration data at the point at which the TMS coil device 20 is currently located, and then accurately displays the TMS coil device 20 on the display 16 using the corrected co-registration data.

In an alternative embodiment, a digitizer pen including trackers is moved from point to point on the scalp 32 in the same manner as described above for the TMS coil device 20. The controller 12 uses information representative of the location of the pen supplied by the camera system 18 to correct an error in the co-registration data at a point where the pen is shown on the display 16 above or below the scalp 32. It is to be understood that the same tracking calibration as discussed above for the TMS coil device 20 can be initially performed for the pen.

In another embodiment, the controller 12 corrects an error in the co-registration while the NBS system 10 is in the offline mode. The outer surface 26 of the TMS coil device 20, or the end of a digitizer pen, is positioned to physically touch the scalp 32. The controller 12 then processes tracking data representative of the location of the TMS coil device 20 or the pen, which is collected at the system 18 that same time, to correct the co-registration data. The controller 12 adjusts the co-registration data using the distance information, for example, as supplied by the user 12 at the device 14, as described above, to cause the TMS coil device 20 or the pen as shown on the display 16 to move towards the approximate center of the head 30 or the brain, or towards the point of the scalp 32 closest to the outer surface 26 of the TMS coil device 16, until any point on the outer surface 26 of the TMS coil device 20 or the end of the pen touches the scalp 32. If the TMS coil device 20 or the pen is shown on the display 16 as being inside the scalp 32, the TMS coil device 20 or the pen is moved in the opposite direction until all points on the outer surface 26 of the TMS coil device 20 or the end of the pen, as shown on the display 16, are outside of the head 30. In a further embodiment, the controller 12 computes the E-field induced on the brain, based on the corrected co-registration data, and stores in its memory data representative of the induced E-field to allow for subsequent analysis.

In a further embodiment, a co-registration procedure performed between the coordinate system used to represent the locations of the TMS coil device and the head and the coordinate system used to represent the head in the MRI image data includes the use of position information collected from trackers on a digitizer pen placed at a plurality of additional points on the subject's scalp 32 which correspond to the same points on a representation on the scalp generated from the MRI image data. The controller 12 performs the co-registration with the additional position information by translating and rotating the coordinate system representative of the MRI image data of the head so that the distance of the additional points to the scalp surface 32, as determined from the MRI image data, is minimized in a least-squares sense. See, for example, K. S. Arun et al, "*Least-squares fitting of two 3-d point sets*," IEEE Transactions on Pattern Analysis and Machine Intelligence, 9(5):698-700 (1987), incorporated by reference herein, which describes rigid co-registration.

In another embodiment, referring again to FIG. 1, the proximity sensor 22 of the TMS coil device 20 detects whether the bottom surface 26 of the casing 21 of the TMS coil device 20 is touching the scalp 32. The proximity sensor 22, for example, is a distance detector that measures distance from the sensor 22 to the scalp 32 or to a reflective marker 24 attached to the head 30. The sensor 22, which has wireless data communication capabilities, wirelessly communicates the information representative of the distance measurement to the wireless device 13 of the controller 12. If the distance information supplied by the sensor 22 is that the distance is other than a value of zero, the controller 12 uses the distance information to correct the co-registration data for the current position of the TMS coil device 20 in relation to the scalp 32.

In one embodiment, the user maintains the TMS coil device 20 above the scalp 32, for example, about 5 mm above the scalp, during NBS. The sensor 22 supplies the distance information to the controller 12, and the controller 12 accordingly accounts for this distance when correcting the co-registration data. The controller 12, for example, performs processing that rotates and translates the representation of the head obtained from the MRI image data and the physical head coordinates until a co-registration is found that maps the outer surface 26 of the TMS coil device 20 at a distance of 5 mm from the scalp surface 32 in the direction along a line extending between respective points on the outer surface 26 and the scalp surface 32 that are closest to each other.

In another embodiment, the controller 12 monitors the display data used to represent the TMS coil device 20 and the scalp 32 on the display 16, and generates an alarm signal at the audio generator 15 to alert the user if the TMS coil device 20 is shown on the display 16 as being located inside the head 30.

Advantageously, the correction of the co-registration data, in accordance with the present invention, in combination with generating an accurate digital representation of the TMS coil device, the scalp surface or any other object of interest, beneficially provides that highly accurate information about the shape and absolute dimensions of the head is available for NBS. The accurate information about the shape and absolute dimensions of the head, for example, can be used to correct for inaccuracies in scaling and for other spatial distortions in a 3D anatomical or functional image of the head obtained from MRI or fMRI image data. For example, inaccuracies in the 3D representation of the head generated from two dimensional ("2D") MRI image data of the head may be corrected by stretching or compressing or by other transformations, such as described in U.S. Patent Publication No. 2006/052687 and U.S. Pat. No. 6,594,516, each of which is incorporated by reference herein. The correction of distortions in the representation of a head generated from the MRI image data using NBS may be applied, for example, in the operating room, planning of surgery etc.

Although preferred embodiments of the present invention have been described and illustrated, it will be apparent to those skilled in the art that various modifications may be made without departing from the principles of the invention.

What is claimed is:

1. A method for correcting an error in positioning a representation of a tracked device in relation to a representation of a scalp surface of a head, comprising:
    supplying information representative of an actual distance between the tracked device and the scalp surface, wherein the tracked device and the scalp surface representations are generated in connection with performing navigated brain stimulation ("NBS") using a transcranial magnetic stimulation ("TMS") induction coil device, and
    correcting co-registration data using the distance information, wherein the co-registration data is generated from correlating a coordinate system used to represent the head of the subject in image data with a coordinate system used to represent the location of reflective trackers affixed to the scalp surface of the subject and the tracked device.

2. The method of claim 1, wherein image data is magnetic resonance imaging data.

3. The method of claim 1, wherein the distance information is automatically determined.

4. The method of claim 3, wherein the tracked device is a TMS coil device and a proximity sensor on the TMS coil device generates the distance information.

5. The method of claim 4, wherein the proximity sensor measures a distance between a point on the TMS coil device and a point on the scalp surface.

6. The method of claim 1, wherein the distance information is provided by a user.

7. The method of claim 1 further comprising:
    displaying the representation of the tracked device in relation to the representation of the scalp surface on a display using the corrected co-registration data.

8. The method of claim 1, wherein the tracked device is a TMS coil device and wherein the distance information is generated while a user operates the TMS coil device to stimulate a target site on a brain of the subject.

9. The method of claim 1, wherein the tracked device is a TMS coil device and wherein the distance information is generated while a user moves the TMS coil device in relation to the head without stimulating the brain.

10. The method of claim 1, wherein the tracked device is a TMS coil device and wherein the correcting of the co-registration data is performed while a user operates the TMS coil device to stimulate target sites on a brain of the subject.

11. The method of claim 1, wherein the tracked device is a TMS coil device and wherein the correcting of the co-registration data is performed while a user moves the TMS coil device in relation to the head without stimulating the brain.

12. The method of claim 1 further comprising:
    a user of the tracked device observing the position of the representation of the tracked device in relation to the representation of the scalp surface on a NBS display; and
    the user supplying the distance information if the observed position is different than an actual position of the tracked device in relation to the scalp surface.

13. The method of claim 1, wherein the actual position of the tracked device is touching the scalp surface.

14. The method of claim 1 wherein the co-registration data is generated from tracking information representative of the location of reflective trackers affixed to a digitizer pen when the pen is positioned at predetermined points along the scalp surface.

15. The method of claim 1, wherein the co-registration data is generated from a plurality of coordinate system correlations and the correction of the co-registration data using the distance information corrects at least one of the coordinate system correlations.

16. The method of claim 1, wherein the tracked device is a TMS coil device, the method further comprising:
    generating an audible alert if the representation of the TMS coil device positions a point on the representation of the TMS coil device within the head, in relation to the representation of the scalp surface of the head.

17. The method of claim 1 further comprising:
    correcting the image data representative of the head based on the corrected co-registration data.

18. The method of claim 17 further comprising:
    displaying the representation of the head generated from the image data as corrected by the corrected co-registration data.

19. An apparatus for correcting an error in positioning a representation of a tracked device in relation to a representation of a scalp surface of a head, comprising:
    a processor for performing a navigated brain stimulation NBS process including the steps of:
        receiving information representative of an actual distance between the tracked device and the scalp surface at the processor; and
        correcting co-registration data using the distance information, wherein the co-registration data is generated from correlating a coordinate system used to represent the head of the subject in image data with a coordinate system used to represent the location of reflective trackers affixed to the scalp surface of the subject and the tracked device,
    wherein the tracked device and the scalp surface representations are generated in connection with performing NBS using a transcranial magnetic stimulation ("TMS") induction coil device.

20. The apparatus of claim 19, wherein image data is magnetic resonance imaging data.

21. The apparatus of claim 19 further comprising:
    at least one of an input device and proximity sensor coupled to the processor and for supplying the processor with the distance information.

22. The apparatus of claim 21, wherein the proximity sensor automatically determines the distance information.

23. The apparatus of claim 21, wherein the tracked device is a TMS coil device and wherein the proximity sensor is on the TMS coil device and measures a distance between a point on the TMS coil device and a point on the scalp surface.

24. The apparatus of claim 21, wherein the input device is operable by a user for supplying the distance information to the processor.

25. The apparatus of claim 19 further comprising:
a display coupled to the processor, where the display is for displaying the representation of the tracked device in relation to the representation of the scalp surface based on the corrected co-registration data.

26. The apparatus of claim 19, wherein the tracked device is a TMS coil device and wherein the distance information is received at the processor while a user operates the TMS coil device to stimulate a target site on a brain of the subject.

27. The apparatus of claim 19, wherein the tracked device is a TMS coil device and wherein the distance information is received at the processor while a user moves the TMS coil device in relation to the head without stimulating the brain.

28. The apparatus of claim 19, wherein the tracked device is a TMS coil device and wherein the correcting of the co-registration data is performed while a user operates the TMS coil device to stimulate target sites on a brain of the subject.

29. The apparatus of claim 19, wherein the tracked device is a TMS coil device and wherein the correcting of the co-registration data is performed while a user moves the TMS coil device in relation to the head without stimulating the brain.

30. The apparatus of claim 19 further comprising:
an input device and a display coupled to the processor, wherein the processor receives the distance information from the input device based on entry of data at the input device, wherein the position of the representation of the tracked device in relation to the representation of the scalp surface is shown on the NBS display, and wherein the data entry by the user at the input device is performed if the user observes on the display that the representative position of the tracked device in relation to the scalp surface is different than an actual position of the tracked device in relation to the scalp surface.

31. The apparatus of claim 19, wherein the actual position of the tracked device is touching the scalp surface.

32. The apparatus of claim 19 further comprising:
a digitizer pen including reflective trackers, wherein the co-registration data is generated from tracking information representative of the location of the pen reflective trackers when the pen is positioned at predetermined points along the scalp surface.

33. The apparatus of claim 19, wherein the co-registration data is generated from a plurality of coordinate system correlations and the correction of the co-registration data using the distance information corrects at least one of the coordinate system correlations.

34. The apparatus of claim 19, wherein the tracked device is a TMS coil device, and the apparatus further comprises:
an audible sound generator coupled to the processor, wherein the sound generator generates an audible alert if a point on the TMS coil device representation is positioned within the head, in relation to the representation of the scalp surface of the head.

35. The apparatus of claim 19 further comprising:
a display coupled to the processor and for displaying the representations of the tracked device and the head, wherein the processor corrects the image data representative of the head based on the corrected co-registration data and causes display of a corrected, image data representation of the head on the display.

\* \* \* \* \*